(12) United States Patent
Morishita et al.

(10) Patent No.: US 9,012,417 B2
(45) Date of Patent: Apr. 21, 2015

(54) TOPICAL ADMINISTRATION OF NF-KAPPAB DECOY TO TREAT ATOPIC DERMATITIS

(75) Inventors: Ryuichi Morishita, Osaka (JP); Motokuni Aoki, Osaka (JP); Toshio Ogihara, Osaka (JP); Yasufumi Kaneda, Osaka (JP); Hiroshige Nakamura, Osaka (JP)

(73) Assignee: Anges MG, Inc., Osaka (JP)

( * ) Notice: Subject to any disclaimer, the term of this patent is extended or adjusted under 35 U.S.C. 154(b) by 789 days.

(21) Appl. No.: 10/468,717

(22) PCT Filed: Feb. 6, 2002

(86) PCT No.: PCT/JP02/00990
§ 371 (c)(1),
(2), (4) Date: Aug. 20, 2003

(87) PCT Pub. No.: WO02/066070
PCT Pub. Date: Aug. 29, 2002

(65) Prior Publication Data
US 2004/0162251 A1  Aug. 19, 2004

(30) Foreign Application Priority Data
Feb. 20, 2001 (JP) .................. 2001-44350

(51) Int. Cl.
*A61K 48/00* (2006.01)
*A61K 31/711* (2006.01)
*A61K 38/17* (2006.01)
*C12N 15/113* (2010.01)

(52) U.S. Cl.
CPC .......... *A61K 31/711* (2013.01); *A61K 38/1709* (2013.01); *C12N 15/113* (2013.01); *C12N 2310/13* (2013.01)

(58) Field of Classification Search
USPC ........... 514/44; 435/455; 536/24.1, 24.5, 23.1
See application file for complete search history.

(56) References Cited

U.S. PATENT DOCUMENTS

| | | | |
|---|---|---|---|
| 2,361,756 A * | 10/1944 | Fiero .............................. | 514/783 |
| 4,301,145 A * | 11/1981 | Cestari ......................... | 424/78.07 |
| 4,427,670 A * | 1/1984 | Ofuchi et al. ................. | 514/174 |
| 5,849,903 A * | 12/1998 | Pietrzkowski et al. ...... | 536/24.5 |
| 5,869,088 A * | 2/1999 | Hosokawa et al. ........... | 424/449 |
| 6,262,033 B1 * | 7/2001 | Morishita et al. .............. | 514/44 |
| 6,399,376 B1 * | 6/2002 | Medford et al. ............. | 435/375 |
| 6,410,516 B1 | 6/2002 | Baltimore et al. | |
| 6,747,014 B2 * | 6/2004 | Teng et al. ....................... | 514/44 |
| 7,871,983 B2 | 1/2011 | Morishita et al. | |
| 2003/0013195 A1 * | 1/2003 | Kaneda ......................... | 435/456 |
| 2004/0072726 A1 * | 4/2004 | Morishita et al. ................. | 514/2 |
| 2004/0109843 A1 * | 6/2004 | Morishita et al. ............ | 424/85.1 |
| 2004/0162251 A1 | 8/2004 | Morishita et al. | |
| 2004/0229833 A1 * | 11/2004 | Dzau et al. ...................... | 514/44 |

FOREIGN PATENT DOCUMENTS

| | | | |
|---|---|---|---|
| EP | 0603405 A1 * | 6/1994 | |
| EP | 824918 A1 * | 2/1998 | ............. A61K 31/70 |
| JP | 2001-055331 | 2/2001 | |
| JP | 3778357 | 3/2006 | |
| JP | 2006-089475 | 4/2006 | |
| JP | 2006-111591 | 4/2006 | |
| WO | WO 95/11687 | 5/1995 | |
| WO | WO 02/29044 | 4/2002 | |

OTHER PUBLICATIONS

Abeyama et al. A role for NF-KappaB-dependent gene transactivation in sunburn. The Journal of Clinical Investigation, vol. 105, No. 12, pp. 1751-1759, Jun. 2000.*
Bene et al. Subcellular localization as a limiting factor for utilization of decoy oligonucleotides.☐☐Nucleic Acids Res. vol. 32, No. 19, p. e142, Oct. 2004.*
Griesenbach et al. Cytoplasmic deposition of NFkappaB decoy oligonucleotides is insufficient to inhibit bleomycin-induced pulmonary inflammation. Gene Ther. vol. 9, No. 16, pp. 1109-1115, Aug. 2002.*
Khaled et al. Use of phosphorothioate-modified oligodeoxynucleotides to inhibit NF-kappaB expression and lymphocyte function. Clin Immunol Immunopathol. vol. 86, No. 2, pp. 170-179, Feb. 1998.*
Lebruska et al. Selection and characterization of an RNA decoy for transcription factor NF-kappa B. Biochemistry. vol. 38, No. 10, pp. 3168-3174, Mar. 1999.*
Remington et al. The Science and Practice of Pharmacy, 19th Ed. Easton, PA: Mack Publishing Co., 1995, pp. 1399-1404.*
Edwards. Oil & Soap, vol. 17, No. 4, pp. 82-84, 1940.*
Nakagawa et al. Tacrolimus ointment for atopic dermatitis. The Lancet, vol. 344, No. 8926, p. 883, Sep. 1994.*
Yamashita et al. Nuclear factor kappa B mediates interleukin-8 production in eosinophils. nternational Archives of Allergy and Immunology, vol. 120, pp. 230-236, 1999.*
Mehta et al. Intercellular adhesion molecule-1 suppression in skin by topical delivery of anti-sense oligonucleotides. J. Invest. Dermatol. vol. 115, pp. 805-812, 2000.*
Alexeev et al. Localized in vivo genotypic and phenotypic correction of the albino mutation in skin by RNA-DNA oligonucleotide. Nature Biotechnology, vol. 18, pp. 43-47, Jan. 2000.*
Hiroi et al. Effect of tacrolimus hydrate (FK506) ointment on spontaneous dermatitis in NC/Nga mice. Jpn. J. Pharmacol. vol. 76, pp. 175-183, 1998.*

(Continued)

*Primary Examiner* — Jennifer Dunston
(74) *Attorney, Agent, or Firm* — Foley & Lardner LLP

(57) ABSTRACT

A pharmaceutical composition for performing treatment against a skin disease, the pharmaceutical composition comprising at least one decoy and a pharmaceutically acceptable carrier. The at least one decoy may be selected from the group consisting of an NF-κB decoy, a STAT-1 decoy, a GATA-3 decoy, a STAT-6 decoy, an AP-1 decoy and an Ets decoy. The at least one decoy may be an oligonucleotide including at least two decoys bonded to each other, the at least two decoys being selected from the group consisting of an NF-κB decoy, a STAT-1 decoy, a GATA-3 decoy, a STAT-6 decoy, an AP-1 decoy and an Ets decoy. The skin disease may be atopic dermatitis, psoriasis vulgaris, contact dermatitis, keloid, bedsore, ulcerative colitis, or Crohn's disease.

4 Claims, 13 Drawing Sheets
(10 of 13 Drawing Sheet(s) Filed in Color)

(56) References Cited

OTHER PUBLICATIONS

TransAM™ NF-κB p65/ NF-κB p50/ NF-κB p52 Transcription Factor Assay Kits (version G), printed from www.activemotif.com, pp. 1-20, 2009.*

Linker et al. Cloning of the murine relA (p65 NF-kappa B) gene and comparison to the human gene reveals a distinct first intron. Gene, vol. 176, pp. 119-124, 1996.*

Nakamura, H., Aoki, M., Tamai, K., Oishi, M., Ogihara, T., Kaneda, Y., and Morishita, R. Preventiona nd Regression of Atopic Dermatitis by Ointment Containing NFκB Decoy Oligodeoxynucleotides in NC/Nga Atopic Mice Model. The Journal of Allergy and Clinical Immunology, vol. 109, No. 1 Supplement, pp. S86-S87, Jan. 2002.*

Bielinska et al., "Regulation of gene expression with double-stranded phosphorothiolate oligonucleotides," *Science*, 250:997-1000 (1990)

Cho-Chung et al., "Oligonucleotides as transcription factor decoys," *Current Opinion in Molecular Therapeutics*, 1(3):386-392 (1999).

Giannoukakis et al., "Prolongation of cardiac allograft survival using dendritic cells treated with NF-κB decoy oligodeoxyribonucleotides," *Molecular Therapy*, 1(5):430-437 (2000).

Kraft and Bieber, "FcεRI-mediated activation of transcription factors in antigen-presenting cells," *Int. Arch. Allergy Immunol.*, 125:9-15 (2001).

Kulms and Schwarz, "Molecular mechanisms of UV-induced apoptosis," *Photodermatology, Photoimmuology & Photomedicine*, 16:195-201 (2000).

Muhpy et al., "The molecular determinants of sunburn cell formation," *Experimental Dermatology*, 10:155-160(2001).

Ardaillou et al., "Production et activite proinflammatoire de necrose tumorale alpha dans le glomerule," *L'Academie Nationale de Medecine*, 179:103-116 (1995).).

Bond et al., "Nuclear factor κB activity is essential for matrix metalloproteinase-1 and -3 upregulation in rabbit dermal fibroblasts," *Biochemical and Biophysical Research Communications*, 264:561-567 (1999).

Bond et al., "Synergistic upregulation of metalloproteinase-9 by growth factors and inflammatory cytokines: an absolute requirement for transcription factor NF-κB," *FEBS Letter*, 435:29-34 (1998).

Brunner et al., "Single bilayer vesicles prepared without sonication physico-chemical properties," *Biochimica et Biophysica Acta Biomembranes*, 455(2):322-331 (1976).

Danning et al., "Macrophage-derived cytokine and nuclear factor κB p65 expression in synovial membrane and skin of patients with psoriatic arthritis," *Arthritis and Rheumatism*, 43(6)1244-1256 (2000).

Deamer, "Preparation and properties of ether-injection liposomes," *Annals of the New York Academy of Sciences*, 308:250-258 (1978).

Denhardt, "Oncogene-initiated aberrant signaling engenders the metastatic phenotype: synergistic transcription factor interactions are targets for cancer therapy," *Critical Reviews in Oncogenesis*, 7(3&4):261-269 (1996).

Eberhardt et al., "Amplification of IL-1β-induced matrix metalloproteinase-9 expression by superoxide in rat glomerular mesangial cells is mediated by increased activities of NF-κB and activating protein-1 and involves activation of the mitogen-activated protein kinase pathways," *Journal of Immunology*, 165:5788-5797 (2000).

Goebeler et al., "Activation of nuclear factor- and gene expression in human endothelial cells by the common haptens nickel and cobalt," *The Journal of Immunology*, 155:2459-2467 (1995).

Hidi et al., "Role of B7-CD28/CTLA-4 costimulation and NF-κB in allergen-induced T cell chemotaxis by IL-16 and RANTES," *The Journal of Immunology*, 164:412-418 (2000).

Kim et al., "Lipopolysaccharide activates matrix metalloproteinase-2 in endothelial cells through an NF-κB-dependent pathway," *Biochemical and Biophysical Research Communications*, 269:401-405 (2000).

Kuner et al., "β-amyloid binds to p75$^{NTR}$ and activates NFκB in human nueroblastoma cells," *Journal of Neuroscience Research*, 54:798-804 (1998).

Lin et al., "Cancer chemoprevention by tea polyphenols through mitotic signal transduction blockade," *Biochemical Pharmacology*, 58:911-915 (1999).

Mathieu et al., "The glucocorticoid receptor gene as a candidate for gene therapy in asthma," *Gene Therapy*, 6:245-252 (1999).

Mori et al., "Transcriptional control of the IL-5 gene by human helper T cells: IL-5 synthesis is regulated independently from IL-2 or IL-4 synthesis," *Journal of Allergy and Clinical Immunology*, 102:S429-S436 (1999).

Nakamura et al., "Upregulation of the transcription factor GATA-3 in upper airway mucosa after in vivo and in vitro allergen challenge," *Journal of Allergy and Clinical Immunology*, 105:1146-1152 (2000).

O'Garra, "Checkpoints for regulation of development and IFN-γ production by Th1 cells in TCR-transgenic models," *Immunology Letters*, 65:41-44 (1999).

Rayet et al., "Aberrant *rel/nfkb* genes and activity in human cancer," *Oncogene*, 18:6938-6947 (1999).

Royds et al., "Response of tumour cells to hypoxia: Role of p53 and NFκB," *Journal of Clinical Pathology: Molecular Pathology*, 51:55-61 (1998).

Szoka et al., "Preparation of unilamellar liposomes of intermediate size (0.1-0.2μm) by a combination of reverse phase evaporation and extrusion through polycarbonate membranes," *Biochimica et Biophysica Acta Biomembranes*, 601(3):559-571 (1980).

Tomita et al., "Transcription factor decoy for NFκB inhibits cytokine and adhesion molecule expressions in synovial cells derived from rheumatoid arthritis," *British Society for Rheumatology*, 39:749-757 (2000).

Tomita et al., "Transcription factor decoy for NFκB inhibits TNF-α-induced cytokine and adhesion molecule expression in vivo," *Gene Therapy*, 7:1326-1332 (2000).

Vestergaard et al., "Overproduction of the Th2-specific chemokines in NC/Nga mice exhibiting atopic dermatitis-like lesions," *The Journal of Clinical Investigation*, 104(8)1097-1105 (1999).

Wang et al., "Targeted disruption of Stat6 DNA binding activity by an oligonucleotide decoy blocks Il-4-driven $T_H2$ cell response," *Blood*, 95:12498-1257 (2000).

Yanagihara et al., "Involvement of nuclear factor—κB activation in IgE synthesis in human B cells," *Journal of Allergy and Clinical Immunology*, 98:S224-S229 (1996).

Zhang et al., Inhibition of allergic inflammation in a murine model of asthma by expression of a dominant-negative mutant of GATA-3), *Immunity*, 11:473-482 (1999).

M. Foldvari, "Effect of vehicle on topical liposomal drug delivery: petrolatum bases," J. Microencapsulation, 13(5):589-600 (1996).

Neish et al., "Functional Analysis of the Human Vascular Cell Adhesion Molecule 1 Promoter," *J. Exp. Med.*, vol. 176, pp. 1583-1593, Dec. 1992.

Higgins et al., "Antisense inhibition of the p65 subunit of NF-κB blocks tumorigenicity and causes tumor regression," *Proc. Natl. Acad. Sci. USA*, vol. 90, pp. 9901-9905, Nov. 1993.

Examiner's Answer issued Dec. 11, 2008 in U.S. Appl. No. 10/366,718 (US 2004/0162250).

Office Action issued Nov. 27, 2007, by the Examiner in U.S. Appl. No. 10/366,718 (US 2004/0162250).

Nakamura et al., "Prevention and regression of atopic dermatitis by ointment containing NF-κB decoy oligodeoxynucleotides in NC/Nga atopic mouse model," *Gene Therapy*, vol. 9, pp. 1221-1229, 2002.

Yakoseki et al., "cis Element Decoy Against Nuclear Factor—NF-κB Attenuates Development of Experimental Autoimmune Myocarditis in Rats," *Circulation Research*, Nov. 9, 2001, pp. 899-906.

Office Action issued Jul. 30, 2009 by the Examiner in U.S. Appl. No. 10/850,994 (US 2004-0229833).

Office Action issued Dec. 15, 2008 by the Examiner in U.S. Appl. No. 10/850,994 (US 2004-0229833).

Office Action issued Apr. 30, 2008 by the Examiner in U.S. Appl. No. 10/850,994 (US 2004-0229833).

Office Action issued May 31, 2007 by the Examiner in U.S. Appl. No. 10/850,994 (US 2004-0229833).

Office Action issued Sep. 21, 2006 by the Examiner in U.S. Appl. No. 10/850,994 (US 2004-0229833).

(56) References Cited

OTHER PUBLICATIONS

Office Action issued Jun. 17, 2005 by the Examiner in U.S. Appl. No. 10/850,994 (US 2004-0229833).

Office Action issued Sep. 22, 2004 by the Examiner in U.S. Appl. No. 10/850,994 (US 2004-0229833).

Paquet et al., "Would Cyclosporin A Be Beneficial to Mitigate Drug-Induced Toxic Epidermal Necrolysis," *Dermatology*, vol. 198, pp. 198-202, 1998.

Novartis, "Neoral™," Product Information brochure, revised Oct. 2009.

Weinstein, "Oral and Topical Cyclosporine Therapy for Psoriasis," *The Western Journal of Medicine*, vol. 151, No. 6, pp. 651-652, Dec. 1989.

Duell et al., "Cyclosporine a Metabolism by Cytochrome P-450III Occurs in Microsomes from Rat Liver but Not from Normal Epidermis or Psoriatic Lesions," *The Journal of Investigative Dermatology*, vol. 96, No. 6, pp. 827-831, Jun. 1991.

Cole et al., The effect of topical cyclosporine A on the elicitation phase of allergic contact dermatitis, *Contact Dermatitis*, vol. 19, pp. 129-132, 1988.

De Rie et al., "Lack of Efficacy of Topical Cyclosporin A in atopic dermatitis and Allergic Contact Dermatitis," *Acta Derm. Venereol. (Stockh)*, vol. 71, pp. 452-454, 1991.

Bos et al., "The 500 Dalton rule for skin penetration of chemical compounds and drugs," *Exp. Dermatol.*, vol. 9, pp. 165-169, 2000.

Brand, "Topical and transdermal delivery of antisense oligonucleotides," *Current Opinion in Molecular Therapeutics*, vol. 3, No. 3, pp. 244-248, 2001.

Fan et al., "Effects of Dietary Restriction on Spontaneous Dermatitis in NC/Nga Mice," *Exp. Biol. Med.*, vol. 226, No. 11, pp. 1045-1050, 2001.

Takano et al., "Di-(2-ethylhexyl) Phthalate Enhances Atopic Dermatitis-Like Skin Lesions in Mice," *Environmental Health Perspectives*, vol. 114, No. 8, pp. 1266-1269, Aug. 2006.

Astellas Pharma Manufacturing, Inc., "Protopic®," Product Information brochure, 2006.

Decision on Appeal issued on Jun. 8, 2010 by the Board of Patent Appeals and Interferences in U.S. Appl. No. 10/366,718 (US 2004/0162250).

Record of Oral Hearing issued on Jun. 25, 2010 by the Board of Patent Appeals and Interferences in U.S. Appl. No. 10/366,718 (US 2004/0162250).

Notice of Allowance issued on Sep. 13, 2010 by the Examiner in U.S. Appl. No. 10/366,718 (US 7,871,983).

R. Hidi, et al., "Role of B7-CD28/CTLA-4 Costimulation and NF-κB in Allergen-Induced T Cell Chemotaxis by IL-16 and RANTES," *Journal of Immunology*, 164(1), pp. 412-418 (2000).

* cited by examiner

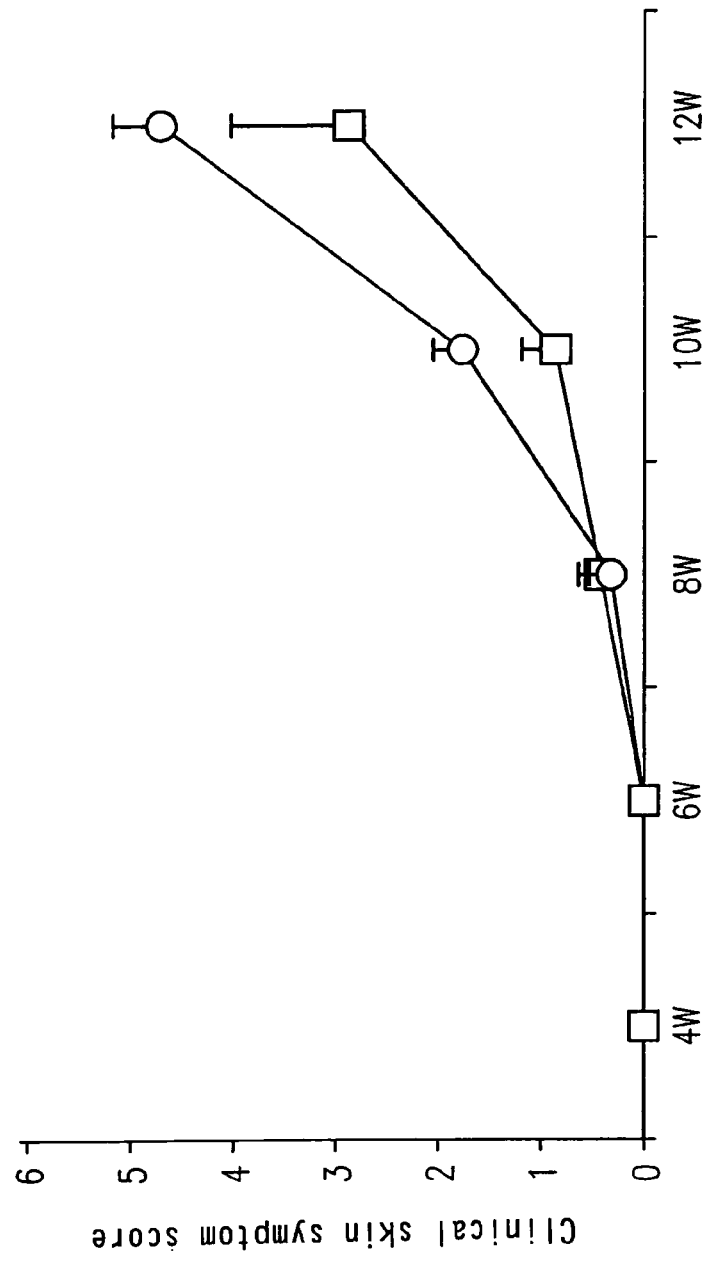

TOPICAL ADMINISTRATION OF NF-KAPPAB DECOY TO TREAT ATOPIC DERMATITIS

TECHNICAL FIELD

The present invention relates to a composition comprising a compound (e.g., a nucleic acid and a homolog thereof) which specifically binds to a site on a chromosome, to which site a transcriptional regulatory factor binds, and a method of using the same. More particularly, the present invention relates to a composition comprising a decoy compound and a method of using the same.

BACKGROUND ART

A variety of diseases including asthma, cancers, heart diseases, aneurysms, autoimmune diseases, and viral infections manifest varying symptoms and signs and yet it has been suggested that an abnormal expression (an overexpression or underexpression) of one or a few proteins is a major etiologic factor in many cases. In general, the expression of those proteins is controlled by a variety of transcriptional regulatory factors such as transcription activating factors and transcription suppressing genes.

A representative transcriptional factor NF-κB is a transcriptional regulatory factor consisting of heterodimers p65 and p50. NF-κB is typically localized in the cytoplasm where NF-κB is bound by its inhibitory factor IκB so that intranuclear movement of NF-κB is prevented. However, when a stimulus, such as cytokine, ischemia, reperfusion, or the like, is applied due to any cause, IκB is degraded after phosphorylation. As a result, NF-κB is activated and transferred into the nucleus. In the nucleus, NF-κB binds to an NF-κB binding site on a chromosome and promotes the transcription of a gene downstream thereof. As genes located downstream of the NF-κB binding site, for example, inflammatory cytokines (e.g., IL-1, IL-6, IL-8, tumor necrosis factor α (TNF α), etc.) and adhesion molecules (e.g., VCAM-1, ICAM-1, etc.) are known.

NF-κB may be involved in the onset of progression of tumor malignancy (Rayet B et al., Oncogene 1999 Nov. 22; 18(49)6938-47); NF-κB is involved in response of tumor cells to hypoxia stress (Royds J A et al., Mol Pathol 1998 April; 51(2):55-61); NF-κB inhibits expression of cytokines and adhesion molecules in synovial membrane cells derived from chronic rheumatoid arthritis patients (Tomita T et al., Rheumatology (Oxford) 2000 July; 39(7):749-57); suppression of coordination between a plurality of transcriptional factors including NF-κB changes the malignant phenotypes of various tumors (Denhardt D. T., Crit. Rev. Oncog., 1996; 7(3-4):261-91); downregulation of NF-κB activity due to green tea polyphenol blocks induction of nitric oxide synthesizing enzyme, and suppresses A431 human epidermoid carcinoma cells (Lin J. K., et al., Biochem. Pharmacol., 1999, Sep. 15; 58(6):911-5); amyloid β peptide observed in the brains of Alzheimer's disease patients binds to 75-kD neurotrophic receptor (p75NTR) in neuroblastoma cells to activate NF-κB in a time-dependent manner and a dose-dependent manner (Kuper P, et al., J. Neurosci. Res., 1998, Dec. 15; 54(6):798-804); TNF-α, which is activated by NF-κB, plays an important role in the onset of glomerulonephritis (Ardaillou et al., Bull. Acad. Natl. Med., 1995, January; 179(1)103-15). NF-κB decoy in vivo blocks expression of cytokines and adhesion molecules in mouse nephritis induced by TNF a (Tomlta N., et al., Gene Ther., 2000, August; 7(15)1326-32); and the like.

It has been suggested that NF-κB suppresses MMP1 and MMP9 which are members of matrix metalloproteinase (MMP) at a transcriptional level (Amplification of IL-1 beta-induced matrix metalloproteinase-9 expression by superoxide in rat glomerular mesangial cells is mediated by increased activities of NF-kappaB and activating protein-1 and involves activation of the mitogen-activated protein kinase pathways. Eberhardt W, Huwiler A, Beck K F, Walpen S, Pfeilschifter J. J Immunol 2000 Nov. 15, 165(10), 5788-97; Nuclear factor kappaB activity is essential for matrix metalloproteinase-1 and -3 upregulation in rabbit dermal fibroblasts. Biochem Biophys Res Commun. Bond M, Baker A H, Newby A C. 1999 Oct. 22, 264(2), 561-7; Synergistic upregulation of metalloproteinase-9 by growth factors and inflammatory cytokines: an absolute requirement for transcription factor NF-kappa B. Bond M, Fabunmi R P, Baker A H, Newby A C. FEBS Lett 1998 Sep. 11, 435(1), 29-34; and Lipopolysaccharide activates matrix metalloproteinase-2 in endothelial cells through an NF-kappaB-dependent pathway. Kim H, Koh G. Biochem Biophys Res Commun. 2000 Mar. 16, 269(2), 401-5).

It is known that in atopic dermatitis pathology or atopic dermatitis model animal, the increase in NF-κB activity induces increase in expression of various cytokines which accompanies infiltration or activation of lymphocytes and thus plays an important role in the onset or progression of the pathology (Role of B7-CD28/CTLA-4 costimulation and NF-kappa B in allergen-induced T cell chemotaxis by IL-16 and RANTES. Hidi R, Riches V, Al-Ali M, Cruikshank W W, Center D M, Holgate S T, Djukanovic R. J Immunol 2000 Jan. 1, 164(1), 412-8; Checkpoints for regulation of development and IFN-γ production by Th1 cells in TCR-transgenic models. Anne O'Garra. Immunology 1999 65, 41-44; Overproduction of Th2-specific chemokines in NC/Nga mice exhibiting atopic dermatitis-like lesions. Christian Vestergaard et al. J Clin Invest 1999 104, 1097-1105; Involvement of nuclear factor-kappa, B activation in IgE synthesis in human B cells. Yanagihara Y, Basaki Y, Ikizawa K, Kajiwara K, Koshio T, Akiyama K. J Allergy Clin Immunol 1996 December 98 (6 Pt 2):S224-9).

It has also been suggested that activation of NF-κB is one of the important mechanisms in psoriasis vulgaris, contact dermatitis, and the like (Macrophage-derived cytokine and nuclear factor kappaB p65 expression in synovial membrane and skin of patients with psoriatic arthritis. Danning C L, Illei G G, Hitchon C, Greer M R, Boumpas D T, McInnes I B Arthritis Rheum 2000 June, 43(6), 1244-56; Activation of nuclear factor-kappa B and gene expression in human endothelial cells by the common haptens nickel and cobalt. Goebeler M, Roth J, Brocker E B, Sorg C, Schulze-Osthoff K. J Immunol 1995 Sep. 1; 155(5):2459-67).

GATA-3 is a transcription factor which plays an important role in the onset and the progression of allergic diseases (Upregulation of the transcription factor GATA-3 in upper airway mucosa after in vivo and in vitro allergen challenge. Nakamura Y, Christodoulopoulos P, Cameron L, Wright E, Lavigne F, Toda M, Muro S, Ray A, Eidelman D H, Minshall E, Hamid Q. J Allergy Clin Immunol 2000 June 105(6Pt1), 1146-52; Inhibition of allergic inflammation in a murine model of asthma by expression of a dominant-negative mutant of GATA-3, Zhang D H, Yang L, Cohn L, Parkyn L, Homer R, Ray P, Ray A, Immunity 1999 October 11(4), 473-82).

STAT-6 is a transcription factor which controls the expression regulation mechanism of IL-4 and reaction of helper T cells by IL-4 (Wang L H, Yang X Y, Kirken R A, Resau J H, Farrar W L. Targeted disruption of stat6 DNA binding activity by an oligonucleotide decoy blocks IL-4-driven T(H)2 cell response. Blood 2000 Feb. 15, 95(4), 1249-57).

AP-1 is a transcription factor which plays an important role in the onset and the progression of allergic diseases (Transcriptional control of the IL-5 gene by human helper T cells: IL-5 synthesis is regulated independently from IL-2 or IL-4 synthesis. Mori A, Kaminuma O, Mikami T, Inoue S, Okumura Y, Akiyama K, Okudaira H. J Allergy Clin Immunol 1999 May 103 (5 Pt2), S429-36; The glucocorticoid receptor gene as a candidate for gene therapy in asthma, Mathieu M, Gougat C, Jaffuel D, Danielsen M, Godard P, Bousquet J, Demoly P, Gene Ther 1999 February, 6(2), 245-52).

Stat-1 and Ets are also transcription factors considered to play an important role in the onset and the progression of allergic diseases.

As described above, transcription factors containing NF-κB have been suggested to be involved in various diseases through expression of various genes under the transcription control thereof, but no method for effective treatment against these diseases has been provided.

DISCLOSURE OF THE INVENTION

The present invention provides a composition containing a decoy compound which is suitable for treating skin diseases including atopic dermatitis, psoriasis vulgaris, contact dermatitis, keloid, bedsore, ulcerative colitis, Crohn's disease, and the like, and a method for using the same.

The present invention provides a composition containing a decoy compound as a main component for treating (curing and preventing) skin diseases and a method for performing treatment against such diseases. The present inventors have found that administration of a decoy compound is effective for treating skin diseases and completed the present invention.

The present invention is directed to a pharmaceutical composition for performing treatment against a skin disease, the pharmaceutical composition comprising at least one decoy and a pharmaceutically acceptable carrier.

Preferably, the at least one decoy is selected from the group consisting of an NF-κB decoy, a STAT-1 decoy, a GATA-3 decoy, a STAT-6 decoy, an AP-1 decoy and an Ets decoy.

Alternatively, the at least one decoy is an oligonucleotide including at least two decoys bonded to each other, the at least two decoys being selected from the group consisting of an NF-κB decoy, a STAT-1 decoy, a GATA-3 decoy, a STAT-6 decoy, an AP-1 decoy and an Ets decoy.

The skin disease maybe atopic dermatitis, psoriasis vulgaris, contact dermatitis, keloid, bedsore, ulcerative colitis, or Crohn's disease.

Preferably, the pharmaceutically acceptable carrier contains petrolatum.

Preferably, the pharmaceutically acceptable carrier is petrolatum, petrolatum containing 5% stearyl alcohol, or petrolatum containing liquid paraffin.

BRIEF DESCRIPTION OF THE DRAWINGS

The patent or patent application file contains at least one drawing executed in color. Copies of this patent or patent application publication with color drawing(s) will be provided to the Patent Office upon request and payment of the necessary fee.

FIG. 2A shows the clinical skin symptom score (protocol 1) which shows an effect of the present invention against atopic dermatitis with time.

BEST MODE FOR CARRYING OUT THE INVENTION

Figure 1:
FIG. 1 is a fluorescent photomicrogragh (×400) of a skin sample from an upper half of the back of a mouse administered with a composition according to the present invention.

The term "decoy" or "decoy compound" refers to a compound which binds to a site on a chromosome, which NF-κB binds to, or a site on a chromosome, which another transcription regulatory factor for a gene controlled by NF-κB (hereinafter referred to as a target binding site) binds to, and antagonizes the binding of NF-κB, Ets, or other transcriptional factors to these target binding sites. Representatively, the decoy or the decoy compound includes a nucleic acid and analogs thereof.

When a decoy is present within a nucleus, the decoy conflicts with a transcription regulatory factor competing for a target binding site, for the transcription regulatory factor. As a result, a biological function which would be generated by binding of the transcription regulatory factor to the target binding site is inhibited. The decoy contains at least one nucleic acid sequence capable of binding to a target binding sequence. A decoy can be used for preparation of a pharmaceutical composition according to the present invention as long as the decoy can bind to a target binding sequence.

Preferable examples of a decoy include, but are not limited to,

| | | |
|---|---|---|
| 5'-CCT-TGA-AGG-GAT-TTC-CCT-CC-3' | (SEQ ID: 1) | (NF-κB decoy); |
| 5'-GAT-CTA-GGG-ATT-TCC-GGG-AAA-TGA-AGC-T-3' | (SEQ ID: 2) | (STAT-1 decoy); |
| 5'-AGC-TTG-AGA-TAG-AGC-T-3' | (SEQ ID: 3) | (GATA-3 decoy); |
| 5'-GAT-CAA-GAC-CTT-TTC-CCA-AGA-AAT-CTA-T-3' | (SEQ ID: 4) | (STAT-6 decoy); |
| 5'-AGC-TTG-TGA-GTC-AGA-AGC-T-3' | (SEQ ID: 5) | (AP-1 decoy); | and

| | | |
|---|---|---|
| 5'-AAT-TCA-CCG-GAA-GTA-TTC-GA-3' | (SEQ ID: 6) | (Ets decoy); | an oligonucleotide containing a complement thereof; a variant thereof; and a compound including one or more of these within a molecule. The oligonucleotide may be a DNA or an RNA. The oligonucleotides may also include a modified nucleic acid and/or pseudonucleic acid therein. Further, these oligonucleotides may be mutants thereof, or compounds containing them therein. The oligonucleotides may have a single strand or double strands, or may be linear or circular. A mutant refers to a nucleic acid having the above-described sequences, a part of which has a mutation, a substitution, an insertion, or a deletion, and which is capable of specifically antagonizing NF-κB, or another transcription regulatory factor for a gene controlled by NF-κB, with respect to the nucleic acid binding site to which the factor binds.

More preferable decoys include double-strand oligonucleotides containing one or a plurality of the above-described nucleic acid sequences, or mutants thereof. Nucleic acids containing one or a plurality of the above-described nucleic acid sequences are called chimera (double) decoy when the number of nucleic acid sequences contained is two, or triple decoy when the number of nucleic acid sequences contained is three, indicating the number of nucleic acid sequences.

The oligonucleotides for use in the present invention include oligonucleotides modified so as to resist in vivo degradation, and the like, such as oligonucleotides (S-oligo) having a thiophosphatediester bond which is a phosphatediester bond whose oxygen atom is replaced with a sulfur atom, oligonucleotides whose phosphatediester bond is substituted with a methylphosphate group having no electronic charge, and the like.

The decoy of the present invention can be produced with chemical or biochemical synthesis methods known in the art. For example, when a nucleic acid is used as a decoy compound, nucleic acid synthesis methods commonly used in genetic engineering can be employed. For example, a DNA synthesizer maybe used to directly synthesize intended decoy nucleic acids. Further, these nucleic acids, nucleic acids containing the nucleic acids, or parts thereof may be synthesized, followed by amplification using a PCR method, a cloning vector, and the like. Furthermore, nucleic acids obtained by these methods are cleaved using a restriction enzyme, or the like, and linked or the like using DNA ligase, or the like to produce an intended nucleic acid. To obtain decoy nucleic acids which are more stable in cells, base, sugar and phosphate portions of the nucleic acids may be subjected to chemical modification, such as alkylation, acylation, or the like.

The present invention provides a pharmaceutical composition comprising the above-described decoy compound alone or in combination with a stabilizing compound, a diluent, a carrier or another component, or a pharmaceutical agent. The pharmaceutical composition of the present invention may be used in such a form that the decoy is taken into cells in an affected part or cells in an intended tissue.

The pharmaceutical composition of the present invention may be administered in any aseptic biocompatible pharmaceutical carrier (including, but not limited to, physiological saline, buffered physiological saline, dextrose, and water). The above-described decoy compound is used in a pharmaceutical composition mixed with an appropriate excipient, an adjuvant, and/or a pharmaceutically acceptable carrier. Such a composition may be administered to patients alone or in combination with another pharmaceutical agent in a pharmaceutical composition. In an embodiment of the present invention, the pharmaceutically acceptable carrier is pharmaceutically inactive.

The administration of the pharmaceutical composition of the present invention is achieved orally or parenterally. Parenteral delivery methods include topical, application to skin, intra-arterial (e.g., directly into tumor, aneurysm, etc.), intramuscular, subcutaneous, intramedullary, into subarachnoid space, intraventricular, intravenous, intraperitoneal, or intranasal administrations.

In addition to a decoy compound, the pharmaceutical composition of the present invention comprises a pharmaceutically acceptable carrier, such as an excipient and other compounds for accelerating the processing of the decoy compound so as to prepare a pharmaceutically acceptable formulation. The further details of techniques for prescription and administration are described in, for example, the latest version of "REMINGTON'S PHARMACEUTICAL SCIENCES" (Maack Publishing Co., Easton, Pa.).

Hereinafter, pharmaceutically acceptable carriers for use in a pharmaceutical composition of the present invention will be categorized by the administration form and described in detail. The compositions are described for illustrative purposes, and the present invention is not limited to these compositions.

A pharmaceutical composition for oral administration may be prepared using a pharmaceutically acceptable carrier well known in the art in an administration form suitable for administration. Such a carrier can be prepared as a tablet, a pill, a sugar-coated agent, a capsule, a liquid, a gel, a syrup, a slurry, a suspension, or the like, which is suited for the patient to take the pharmaceutical composition.

The pharmaceutical composition for oral use may be obtained in the following manner: a decoy compound is combined with a solid excipient as a carrier, the resultant mixture is pulverized if necessary, an appropriate compound is further added if necessary to obtain a tablet or the core of a sugar-coated agent, and the granular mixture is processed. The appropriate excipient may be a carbohydrate or protein filler, including, but not being limited to, the following: sugar including lactose, sucrose, mannitol, or sorbitol; starch derived from maize, wheat, rice, potato, or other plants; cellulose such as methylcellulose, hydroxypropylmethylcellulose, or sodium carboxymethylcellulose; and gum including gum Arabic and gum tragacanth; and protein such as gelatin and collagen. A disintegrant or a solubilizing agent such as crosslinked polyvinyl pyrrolidone, agar, alginic acid or a salt thereof (e.g., sodium alginate) may be used if necessary.

The sugar-coated agent core is provided along with an appropriate coating, such as a condensed sugar solution. The coating may also contain gum arabic, talc, polyvinyl pyrrolidone, carbopolygel, polyethylene glycol, and/or titanium dioxide, a lacquer solution, and an appropriate organic solvent or a solvent mixed solution. To identify a product, or characterize the amount of an active compound (i.e., dose), dye or pigment may be added to tablets or sugar-coated agents.

The pharmaceutical preparation which may be orally used may contain, for example, a soft sealed capsule consisting of a gelatin capsule, gelatin and coating (e.g., glycerol or sorbitol). The gelatin capsule may contain an active component mixed with a filler or binder such as lactose or starch, a lubricant such as talc or magnesium stearate, and optionally a stabilizer. In the soft capsule, the decoy compound may be dissolved or suspended in an appropriate liquid, such as fatty oil, liquid paraffin or liquid polyethylene glycol, with or without a stabilizer.

The pharmaceutical preparation for parenteral administration contains an aqueous solution of an active compound. For the purpose of injection, the pharmaceutical composition of the present invention is prepared in an aqueous solution, preferably Hank's solution, Ringer's solution, or a physiologically suitable buffer such as a buffered physiological saline. The aqueous suspension for injection may contain a substance for increasing the viscosity of a suspension (e.g., sodium carboxymethylcellulose, sorbitol, or dextran). Further, the suspension of the active compound may be prepared as an appropriate oily suspension. Appropriate lipophilic solvents or vehicles include fatty acid such as sesame oil, synthetic fatty acid ester such as ethyl oleate or triglyceride, or liposome. The suspension may contain a stabilizer which allows a high-concentration solution preparation, or an appropriate pharmaceutical agent or reagent for increasing the solubility of the compound, if necessary.

For topical or intranasal administration, an appropriate penetrant for the specific barrier to be penetrated may be used in the preparation. Such a penetrant is generally known in the art.

The pharmaceutical composition of the present invention may be produced using a method similar to method known in the art (e.g., conventional mixing, dissolution, rendering to granules, preparation of a sugar-coated agent, elutriation, emulsification, capsulation, inclusion, or freeze drying).

Preferably, in the case of parenteral administration, such as topical administration to cells of an affected part or cells of an intended tissue, the pharmaceutical composition of the present invention may contain a synthetic or naturally-occurring hydrophilic polymer as a carrier.

Examples of such a hydrophilic polymer include hydroxypropylcellulose and polyethylene glycol. The decoy compound of the present invention may be mixed with the above-described hydrophilic polymer in an appropriate solvent. The solvent may be removed by a method such as air drying. The resultant compound may be shaped into a desired form, such as sheet, and then may be given to a target site. Such a preparation containing a hydrophilic polymer has a small moisture content, and an excellent shelf life, and an excellent retentivity of the decoy compound since the preparation absorbs water to be turned into gel when used. Such a sheet may include a hydrophilic sheet obtained by mixing polyhydric alcohol with a compound similar to the above-described composition components, such as cellulose or starch, or a derivative thereof, a synthetic polymer compound or the like and adjusting the hardness of the sheet.

Such a sheet may be placed in a target site under a laparoscope. Currently, laparoscopic surgery has been dramatically developed as a non-invasive technique. By combining the pharmaceutical composition of the present invention with the laparoscope technique, a method for treatment of diseases, which can be repeatedly used, may be provided.

Alternatively, when a nucleic acid or a modification thereof is employed as a decoy, the pharmaceutical composition of the present invention is advantageously used in a form which is generally used in gene introduction methods, such as a membrane fusion liposome preparation using Sendai virus (HVJ) or the like, a liposome preparation using endocytosis or the like, a preparation containing a cationic lipid such as Lipofectamine (Lifetech Oriental) or the like, or a viral preparation using a retrovirus vector, an adenovirus vector, or the like. Particularly, a membrane fusion liposome preparation is preferable.

The liposome preparation is any of the liposome constructs which are a large unilamellar vesicle (LUV), a multilamellar vesicle (MLV), and a small unilamellar vesicle (SUV). The LUV has a particle system ranging from about 200 to about 1000 nm. The MLV has a particle system ranging from about 400 to about 3500 nm. The SUV has a particle system ranging from about 20 to about 50 nm. In the case of the membrane fusion liposome preparation using Sendai virus or the like, MLV having a particle system ranging from 200 nm to 1000 nm is preferably employed.

There is no particular limitation on a method for producing liposomes as long as the liposomes hold a decoy. The liposomes can be produced by a commonly used method, such as, for example, a reversed phase evaporation method (Szoka, Fetal., Biochim. Biophys. Acta, Vol. 601 559(1980)), an ether infusion method (Deamer, D. W.: Ann. N.Y. Acad. Sci., Vol. 308250(1978)), a surfactant method (Brunner, J et al.: Biochim. Biophys. Acta, Vol. 455 322(1976)), or the like.

Examples of lipids for forming a structure of a liposome include phospholipids, cholesterols, nitrogen lipids, and the like. Generally, phospholipids are preferable, including naturally-occurring phospholipids, such as phosphatidylcholine, phosphatidylserine, phosphatidylglycerol, phosphatidylinositol, phosphatidylethanolamine, phosphatidic acid, cardiolipin, sphingomyelin, egg yolk lecithin, soybean lecithin, lysolecithin, and the like, or the corresponding phospholipids hydrogenated by a commonly used method, and in addition, synthetic phospholipids, such as dicetylphosphate, distearoylphosphatidylcholine, dipalmitoylphosphatidylcholine, dipalmitoylphosphatidylethanolamine, dipalmitoylphosphatidylserine, eleostearoylphosphatidylcholine, eleostearoylphosphatidylethanolamine, eleostearoylphosphatidylserine, and the like.

The lipids including these phospholipids can be used alone or with at least two in a combination. In this case, lipids having an atom group having a positive group, such as ethanolamine, choline, or the like, within the molecule can be used to increase the binding rate of an electrically negative decoy nucleic acid. In addition to the major phospholipids used to form liposomes, an additive, such as cholesterols, stearylamine, α-tocopherol, or the like, which are generally known as an additive for formation of liposomes, can be used.

The thus-obtained liposomes can additionally contain a substance for promoting membrane fusion, such as a membrane fusion promoting protein purified from Sendai virus, inactivated Sendai virus, Sendai virus, or the like, so as to accelerate uptake into cells at an affected site or cells in an intended tissue.

An exemplary method for producing a liposome preparation will be specifically described below. For example, the above-described substance for forming a liposome is dissolved along with cholesterol in an organic solvent, such as tetrahydrofuran, chloroform, ethanol, or the like. The resultant solution is put into an appropriate vessel, followed by removal of the solvent under reduced pressure, thereby forming a film of the liposome forming substance on an inside wall of the vessel. A buffer solution containing a decoy is added to the vessel followed by agitation. The above-described membrane fusion promoting substance is added to the resultant liposome if necessary, followed by isolation of the liposome. The thus-obtained liposome containing the decoy can be suspended in an appropriate solvent or can be freeze-dried and thereafter dispersed in an appropriate solvent. The resultant suspension can be used in treatment. The membrane fusion promoting substance may be added in the interim period after the isolation of the liposome and before use.

The pharmaceutical composition of the present invention includes a composition containing an effective amount of decoy compound which can achieve the intended purpose of the decoy compound. "Therapeutically effective amount" or "pharmacologically effective amount" are terms which are well recognized by those skilled in the art and which refer to an amount of pharmaceutical agent effective for production of an intended pharmacological effect. Therefore, the therapeutically effective amount is an amount sufficient for reducing the manifestation of the disease to be treated. A useful assay for confirming an effective amount (e.g., a therapeutically effective amount) for a predetermined application is to measure the degree of recovery from a target disease. An amount actually administered depends on an individual to be treated. The amount is preferably optimized so as to achieve a desired effect without a significant side effect. The determination of the therapeutically effective dose is within the ability of those skilled in the art.

A therapeutically effective dose of any compound can be initially estimated using either a cell culture assay or any appropriate animal model. The animal model is used to achieve a desired concentration range and an administration route. Thereafter, such information can be used to determine a dose and route useful for administration into humans.

The therapeutically effective amount refers to an amount of a decoy compound which results in amelioration of symptoms or conditions of a disease. The therapeutic effect and toxicity of such a compound may be determined by standard pharmaceutical procedures in cell cultures or experimental animals (e.g., $ED_{50}$, a dose therapeutically effective for 50% of a population; and $LD_{50}$, a dose lethal to 50% of a population). The dose ratio between therapeutic and toxic effects is a therapeutic index, and it can be expressed, as the ratio of $ED_{50}/LD_{50}$. Pharmaceutical compositions which exhibit high therapeutic indices are preferable. The data obtained from cell culture assays and animal studies can be used in formulating a dosage range for use in humans. The dosage of such compounds lies preferably within a range of circulating concentrations that include the $ED_{50}$ with little or no toxicity. Such a dosage may vary within this range depending upon the dosage form employed, the susceptibility of a patient and the route of administration. As an example, the dose of a decoy is appropriately selected depending on the age and other conditions of a patient, the type of a disease, the type of the decoy employed, and the like. For example, in the case of intravascular administration, intramuscular administration, intra-articular administration, or application to the skin, 1 μg to 100 mg can be generally administered once a day to several times a day.

The exact dose is chosen by an individual physician in view of the condition of a patient to be treated. Doses and administration are adjusted to provide a sufficient level of the active portion, or to maintain a desired effect. Additional factors to be considered include the severity of the condition of a disease (e.g., the size and location of a tumor; the age, weight and sex of a patient; a diet-limiting time and frequency of administration, a combination of drugs, reaction susceptibility, and resistance/response to treatment). A sustained action pharmaceutical composition may be administered every 3 to 4 days, every week, or once per two weeks, depending on the half life and clearance rate of a specific preparation. Guidance for specific doses and delivery methods are provided in publications known in the art.

Medicaments containing the thus-obtained decoy as a major component can be administered in various manners, depending on the type of disease, the type of the decoy employed, and the like. For example, the medicament can be intravascularly administered, applied to the site of a disease, administered to the disease site, or intravascularly administered to the disease site, for ischemic diseases, inflammatory diseases, autoimmune diseases, and cancer metastasis and invasion, and cachexia.

More specifically, for example, when PTCA is performed for infarct of an organ, the medicament can be administered into a blood vessel of an affected part at the same time or before or after the PTCA. In organ transplantation or the like, an organ to be transplanted may be treated in advance with a preparation for use in the present invention. Further, for example, the medicament can be infused directly to a joint in the case of chronic articular rheumatism or the like.

In the case of skin diseases, the composition of the present invention is topically administered to an affected portion of the skin in the form of an ointment. Such an ointment is a semisolid dosage form for external application, which has uniform density appropriate for easy application to the skin. The ointment usually contains, as a carrier, fat, fatty oil, lanolin, petrolatum, paraffin, wax, plaster, resin, plastic, glycols, higher alcohol, glycerin, water or emulsifier, and a suspending agent. In the ointment, a decoy compound is uniformly mixed using such a carrier as a base agent. Depending on the type of base agent, the ointment can be in the form of an oil-and-fat type ointment, an emulsion-type ointment, or a water-soluble ointment. The oil-and-fat type ointment contains an animal or plant oil-and-fat and wax, petrolatum, paraffin or the like as a base agent. The emulsion-type ointment has an oil-and-fat type substance and water emulsified with an emulsifier, and may be either of an oil-in-water (O/W) type or a water-in-oil (W/O) type. The oil-in-water type emulsion-type ointment may be hydrophilic. The water-in-oil type emulsion-type ointment, may contain hydrophilic petrolatum or purified lanolin while lacking water phase from the beginning, or may contain water-phase-containing water-absorbing ointment or water-added lanolin. The water-soluble ointment may contain a completely water soluble Macrogol base agent as a main component.

Hereinafter, the present invention will be described by way of examples. These examples are provided for illustrative purpose only, and the present invention is not limited to these examples.

EXAMPLES

The effects of a composition according to the present invention were confirmed by the following procedure.

1. An NF-κB decoy ointment (the composition thereof will be shown in section 2 below) was used. More specifically, an FITC-labeled NF-κB decoy ointment was applied to a mouse to confirm that the NF-κB decoy was introduced into an interstitium of epidermis and intradermal cells with certainty.

FIG. 1 is a fluorescent photomicrogragh (×400) of a skin sample from an upper half of the back of an NC/Nga mouse which was obtained 4 days after the NF-κB decoy ointment labeled with FITC (fluorescent pigment) was applied thereto. As shown in FIG. 1, the entire interstitium of an epidermical cell uniformly emitted fluorescence, and intradermal lymphocytes and folliculus pili-forming cells were colored green with fluorescence. Thus, it was confirmed that the NF-κB decoy was introduced into the interstitium of epidermis and intradermal cells with certainty.

2. Next, NC/Nga mice (atopic spontaneous crisis model) were divided into a group of mice for local administration of an NF-κB decoy ointment (test group) and a group of mice for local administration of a control decoy ointment (control group). These groups of mice were tested to compare the local effect of the NF-κB decoy ointment against atopic dermatitis. Here, in order to obtain a spontaneous crisis ratio of atopic dermatitis in the test mice of 80% to 100%, four-week-old male mice of the above-mentioned system which were fed only with acarid parasitical to human (Sarcoptes) were purchased and used as atopic dermatitis-inducing mice.

The test can be summarized as follows. The above-purchased NC/Nga mice were divided into two groups. One group of mice (group for local administration of an NF-κB decoy ointment) were each locally administered (applied to skin) with an NF-κB decoy ointment having the following composition in accordance with the following protocols (protocols 1 and 2). More specifically, the NF-κB was administered (applied to skin) to the ears, the upper half of the back, and the head of the mice. The other group of mice (group for local administration of a control decoy ointment) were each locally administered with a control decoy ointment having the following composition in a similar manner to the administration to the group for local administration of the NF-κB decoy ointment. The local effects of these types of ointments against the atopic dermatitis were compared, Composition of the NF-κB Decoy Ointment:
NF-κB decoy: 10 mg, stearyl alcohol: 30 mg, petrolatum: 0.6 g.

Composition of the Control Decoy Ointment:
Control decoy: 10 mg, stearyl alcohol: 30 mg, petrolatum: 0.6 g.

Protocol 1:
The NF-κB decoy or the control decoy is administered in the amount of 1 mg per mouse by application. The administration is performed four times (once every 2 to 4 weeks afterbirth), and evaluation of the results is performed at the 12th week after birth.

Protocol 2:
The NF-κB decoy or the control decoy is administered in the amount of 2 mg per mouse by application. The administration is performed once at the 29th week afterbirth, and evaluation is performed at the 30 week after birth.

The local effects of the ointments administered against atopic dermatitis were macroscopically evaluated using a clinical skin symptom score. The local effects were also evaluated microscopically using HE dyeing in accordance with the fixed method.

FIG. 2A shows the average clinical skin symptom score of each group obtained as a result of the local effect test performed in accordance with protocol 1, which shows an effect against atopic dermatitis. As shown in FIG. 2A, the average clinical skin symptom score of six mice from the group for local administration of the NF-κB decoy ointment was lower than that of the group for local administration of the control decoy ointment in 12 weeks after birth. Thus, the effect of long-term administration of the NF-κB decoy ointment was confirmed.

Figure 2B:
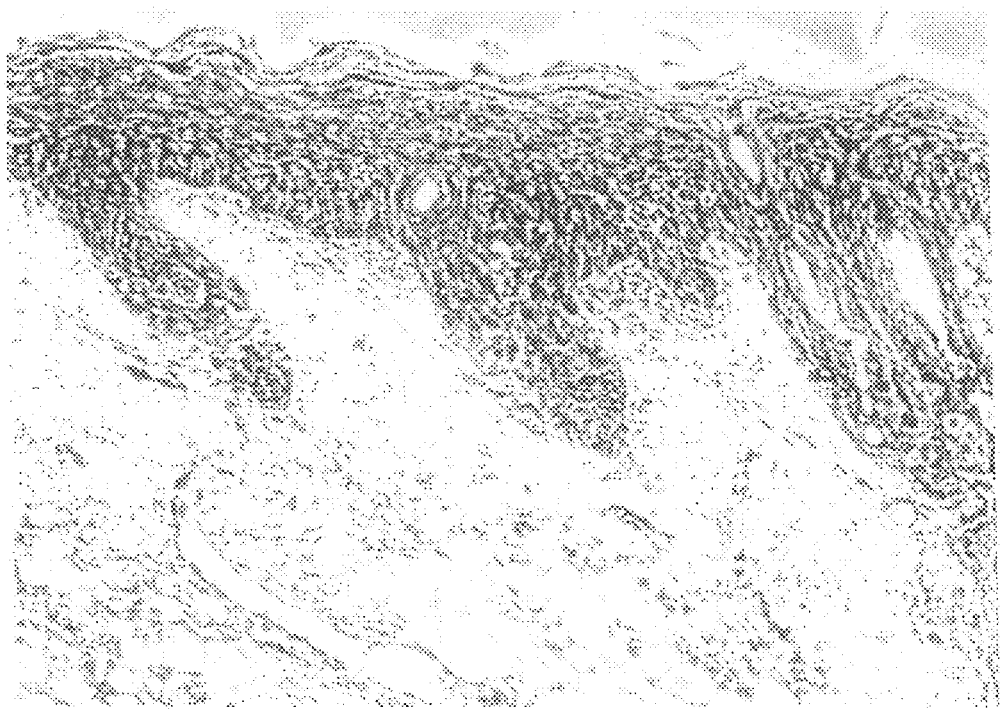
FIG. 2B is a photomicrogragh of an HE-dyed skin sample from an upper half of the back of a mouse of a control group.
Figure 2C:
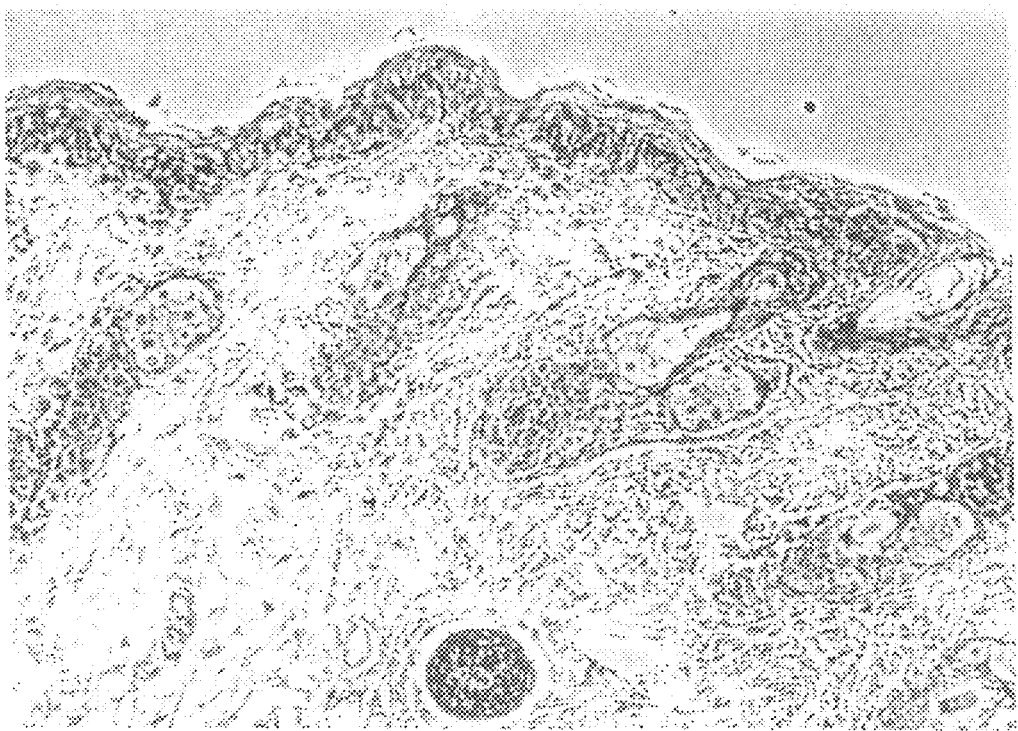
FIG. 2C is a photomicrogragh of an HE-dyed skin sample from an upper half of the back of a mouse of a test group.

FIGS. 2B and 2C are respectively a photograph of a skin sample from the upper half of the back of a mouse from the group for local administration of the control decoy ointment and a photograph of a skin sample from the upper half of the back of a mouse from the group for local administration of the NF-κB decoy ointment (in 12 weeks; HE dyed). As is clear from FIGS. 2B and 2C, in the mouse from the group for local administration of the NF-κB decoy ointment, an improvement in hypertrophy of the epidermis, an improvement in acanthosis, and a reduction in granulose were observed. Thus, it was exhibited that the skin tissues were pathologically improved owing to the infiltration of the NF-κB decoy into the skin.

Figure 2D:
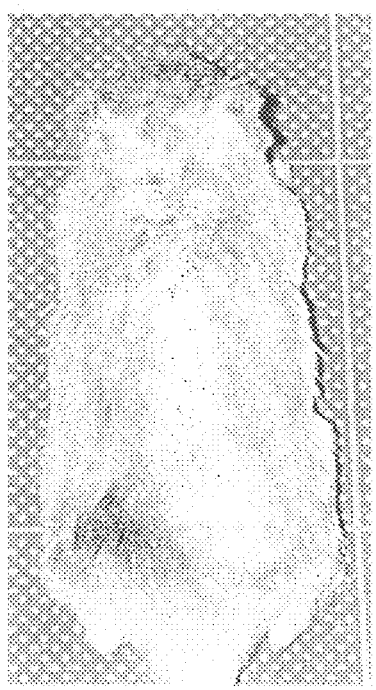
FIG. 2D is a back-view mouse of the control group.
Figure 2E:
FIG. 2E is a back-view of a mouse of the test group.

FIGS. 2D and 2E are respectively a photograph of the back of a mouse from the group for local administration of the control decoy ointment and a photograph of the back of a mouse from the group for local administration of the NF-κB decoy ointment. As can be seen in FIGS. 2D and 2E, the mouse in the group for local administration of the NF-κB decoy ointment exhibits an improvement in eczema accompanying flare as compared to the mouse in the group for local administration of the control decoy ointment. In addition, in the mouse from the group for local administration of the NF-κB decoy ointment, the pruritus impression is observed to have been reduced. These results exhibit that the symptoms of atopic dermatitis were improved owing to the infiltration of the NF-κB decoy into the skin.

Figure 2F:
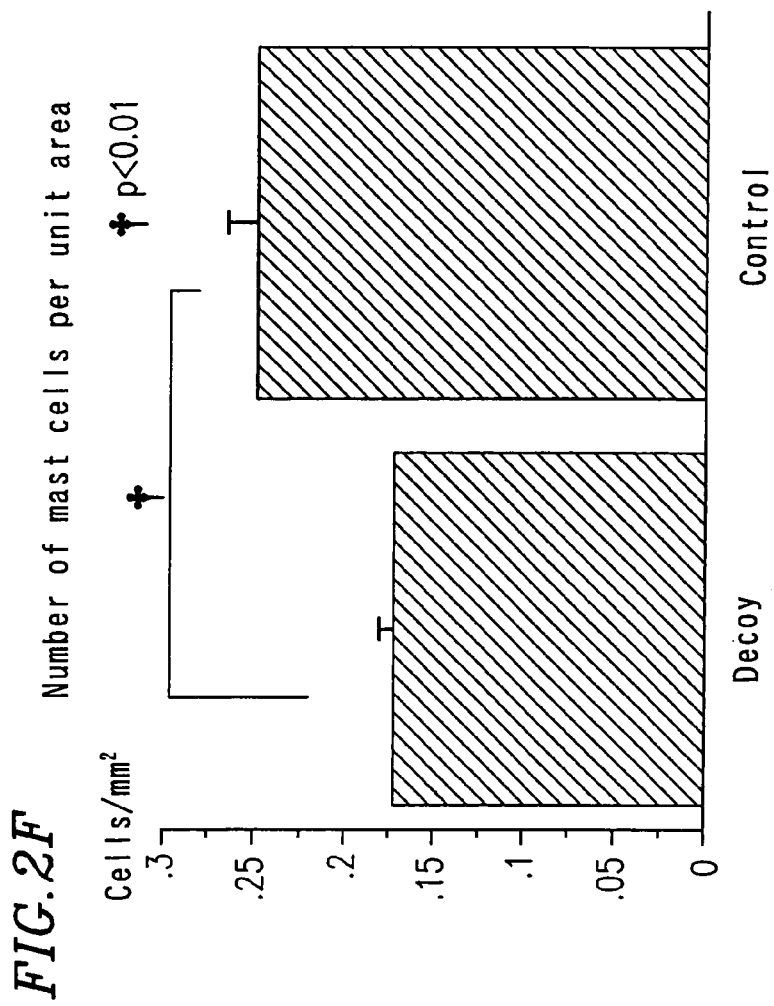
FIG. 2F shows the measurement results of the number of mast cells per unit area of the skin of the mice of the control group and the test group.

FIG. 2F shows the results of measurement of the average number of mast cells per unit area of the skin of the mice from the group for local administration of the NF-κB decoy ointment and the mice from the group for local administration of the control decoy ointment. As is clear from FIG. 2F, the number of mast cells was significantly smaller in the mice from the group for local administration of the NF-κB decoy ointment than in the mice from the group for local administration of the control decoy ointment. Thus, it was exhibited that the NF-κB decoy suppressed the accumulation of mast cells which produce cytokines related to the symptoms of atopic dermatitis.

Figure 3A:
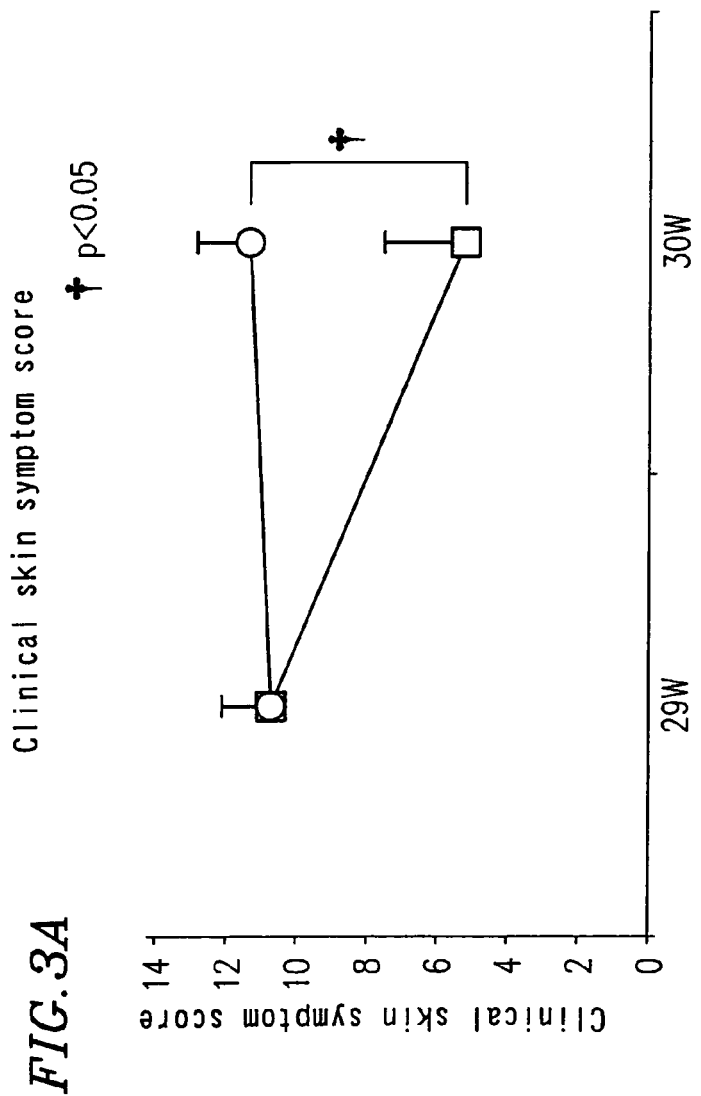
FIG. 3A shows the clinical skin symptom score (protocol 2) which shows an effect of the present invention against atopic dermatitis with time.

FIG. 3A shows the average clinical skin symptom score of each group obtained as a result of the local effect test performed in accordance with protocol 2, which shows an effect against atopic dermatitis. As shown in FIG. 3A, the average clinical skin symptom score of six mice from the group for local administration of the NF-κB decoy ointment was lower than that of the group for local administration of the control decoy ointment in 30 weeks after birth. Thus, the effect of short-term administration of the NF-κB decoy ointment was confirmed.

Figure 3B:
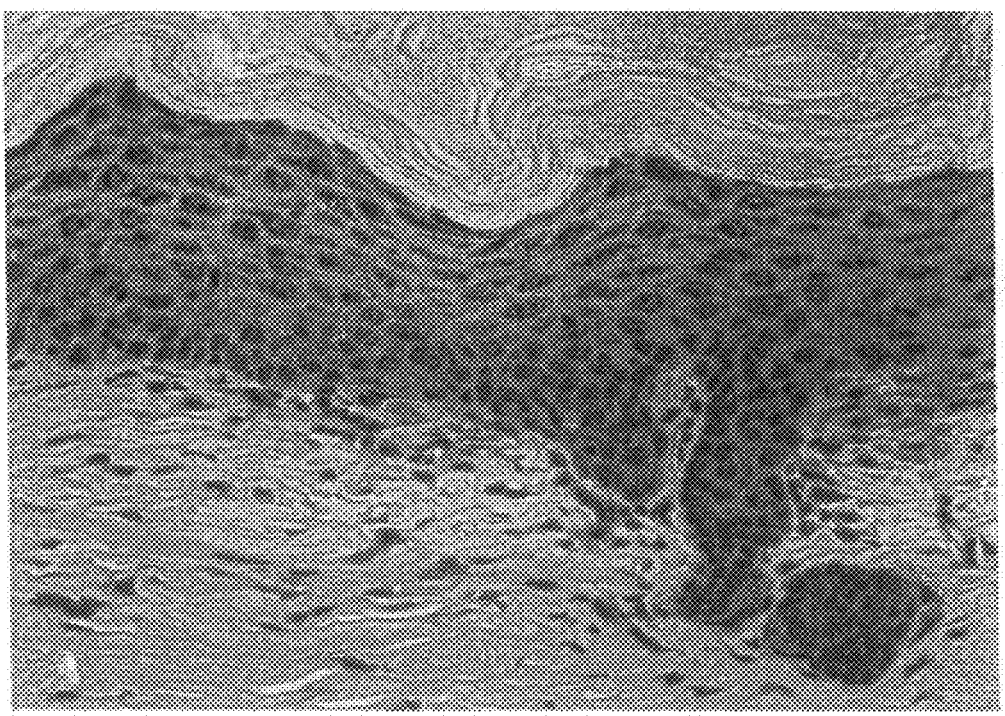
FIG. 3B is a photomicrogragh of an HE-dyed skin sample from an upper half of the back of a mouse of the control group.
Figure 3C:
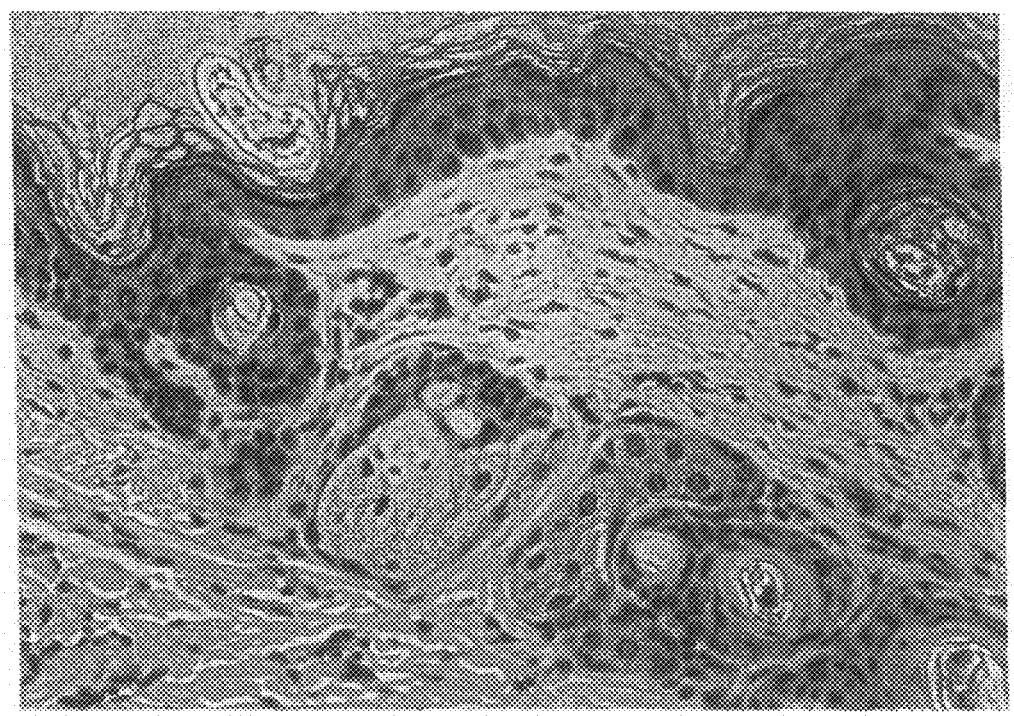
FIG. 3C is a photomicrogragh of an HE-dyed skin sample from an upper half of the back of a mouse of the test group.

FIGS. 3B and 3C are respectively a photograph of a skin sample from the upper half of the back of a mouse from the group for local administration of the control decoy ointment and a photograph of a skin sample from the upper half of the back of a mouse from the group for local administration of the NF-κB decoy ointment (in 12 weeks; HE dyed) obtained as a result of performing the test in accordance with protocol 2. As is clear from FIGS. 3B and 3C, in the mouse from the group for local administration of the NF-κB decoy ointment, an improvement in hypertrophy of the epidermis, an improvement in acanthosis, and a reduction in granulose were observed. Thus, it was exhibited that the skin tissues were pathologically improved owing to the infiltration of the NF-κB decoy into the skin.

Figure 3D:
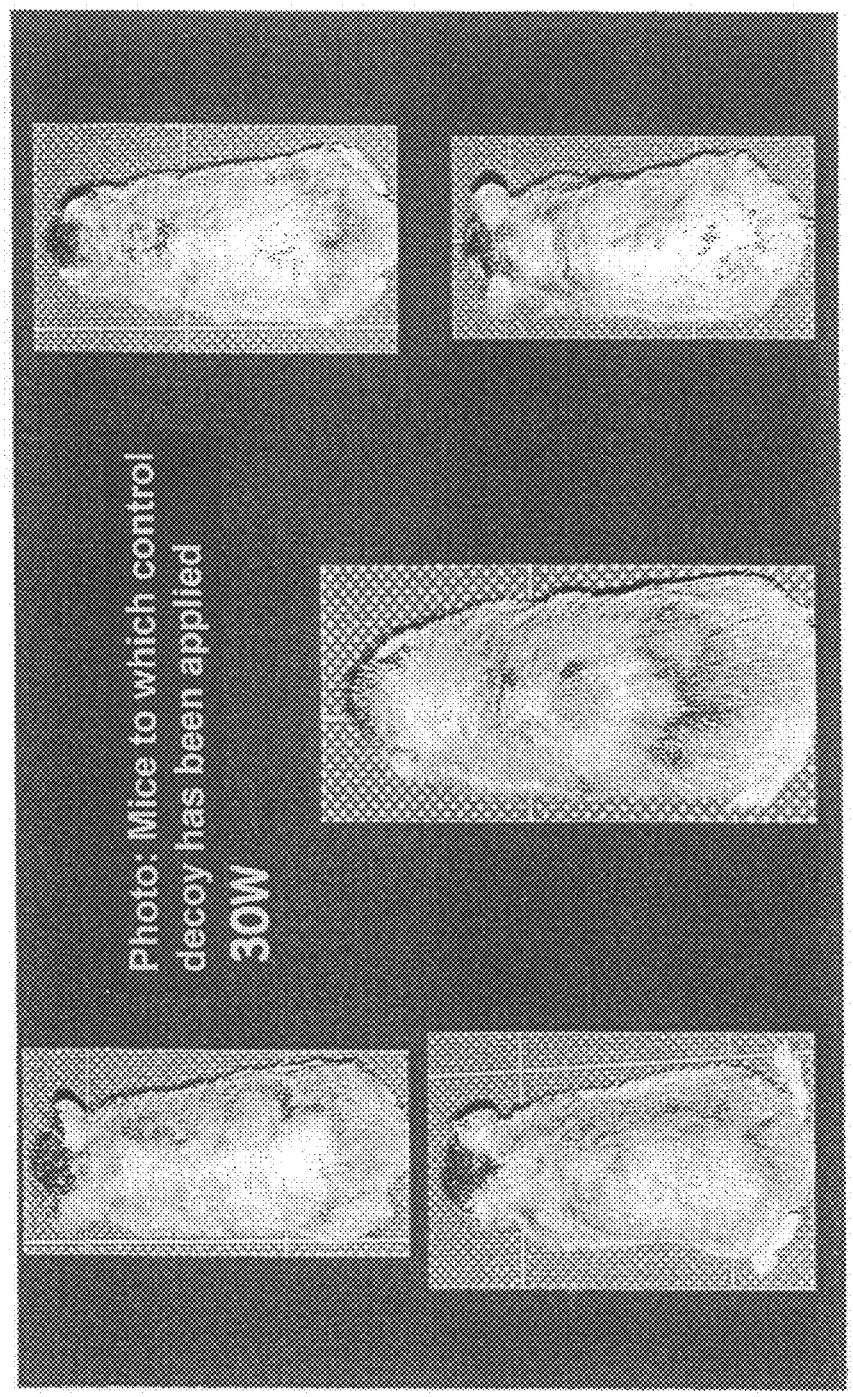
FIG. 3D shows back-view photographs of mice of the control group.
Figure 3E:
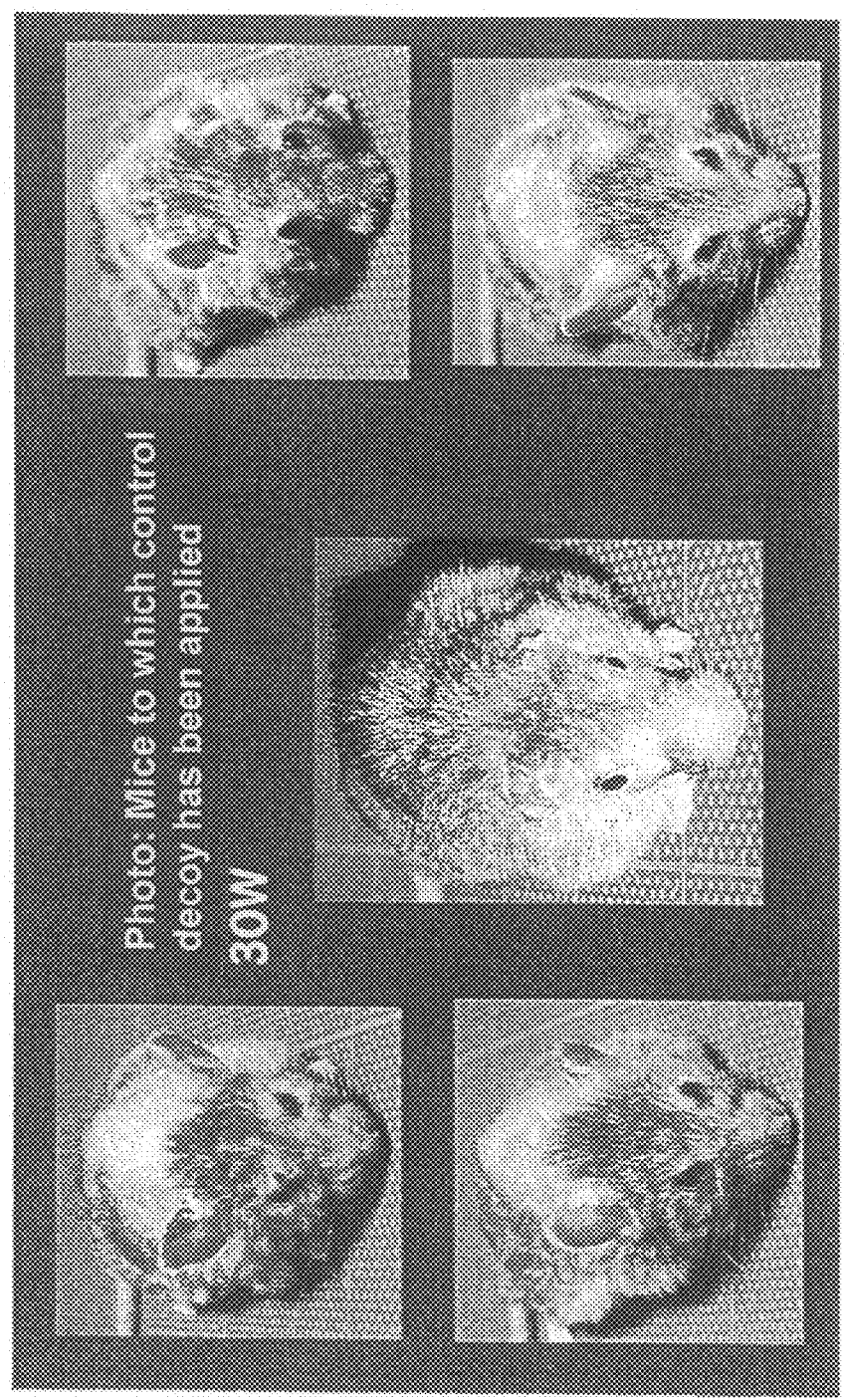
FIG. 3E shows front-view photographs of mice of the control group.

FIG. 3D shows back-view photographs of the mice from the group for local administration of the control decoy ointment, and FIG. 3E shows front-view photographs of the mice from the group for local administration of the control decoy ointment. As can be seen in FIGS. 3D and 3E, the mice of this group show eczema accompanying flare and pruritus impression, which are unique to atopic dermatitis.

Figure 3F:
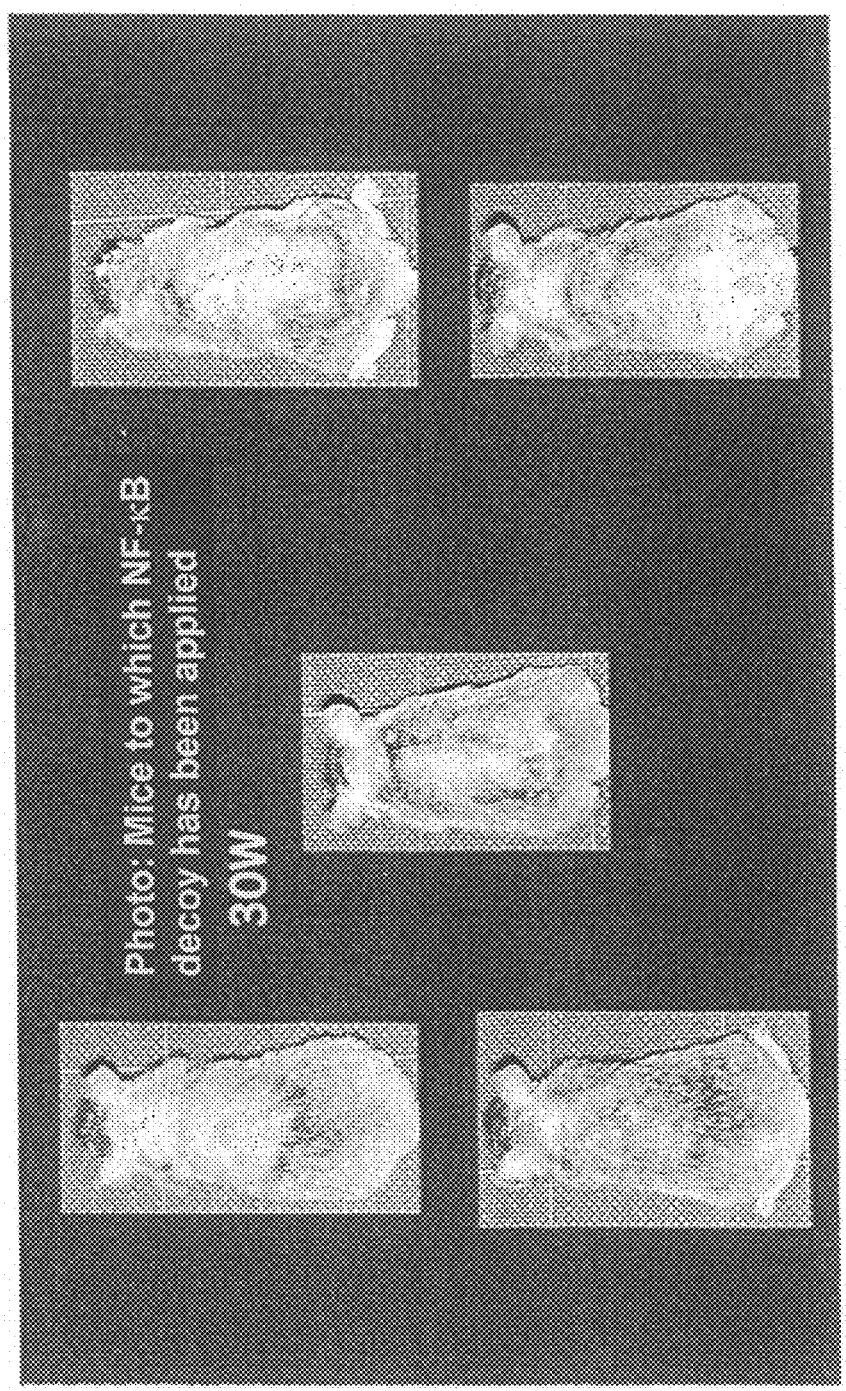
FIG. 3F shows back-view photographs of mice of the test group.
Figure 3G:
FIG. 3G shows front-view photographs of mice of the test group.

FIG. 3F shows back-view photographs of the mice from the group for local administration of the NF-κB decoy ointment, and FIG. 3G shows front-view photographs of the mice from the group for local administration of the NF-κB decoy ointment. As can be seen in FIGS. 3F and 3G, the mice of this group exhibit an improvement in eczema accompanying flare and a reduction in pruritus impression. These results show that the symptoms of atopic dermatitis were improved owing to the infiltration of NF-κB decoy into the skin.,

INDUSTRIAL APPLICABILITY

The present invention provides a composition containing a decoy compound which is suitable for treating skin diseases including atopic dermatitis, psoriasis vulgaris, contact dermatitis, keloid, bedsore, ulcerative colitis, Crohn's disease, and the like, and a method for using the same. The present invention provides a composition containing a decoy compound as a main component and treating (curing and preventing) skin diseases and a method for performing treatment against such diseases.

The invention claimed is:

1. A method for treating atopic dermatitis comprising topically administering a composition comprising:
    (i) an amount of a linear, double-stranded DNA NF-κB decoy effective to treat atopic dermatitis, wherein the decoy competes with the same chromosomal NF-κB binding site as SEQ ID NO:1 and one strand of the decoy comprises the sequence of SEQ ID NO:1; and
    (ii) a pharmaceutically acceptable topical carrier.

2. The method of claim 1, wherein one strand of the double-stranded DNA NF-κB decoy consists of the sequence of SEQ ID NO:1.

3. A method for treating atopic dermatitis comprising topically administering a composition consisting of:
    (i) an amount of a linear, double-stranded DNA NF-κB decoy effective to treat atopic dermatitis, wherein the decoy competes with the same chromosomal NF-κB binding site as SEQ ID NO:1 and one strand of the decoy comprises the sequence of SEQ ID NO:1; and
    (ii) a pharmaceutically acceptable topical carrier that does not include a penetrant.

4. The method of claim 3, wherein one strand of the double-stranded DNA NF-κB decoy consists of the sequence of SEQ ID NO:1.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: NF-kappaB Decoy

<400> SEQUENCE: 1
ccttgaaggg atttccctcc                                                   20

<210> SEQ ID NO 2
<211> LENGTH: 28
<212> TYPE: DNA
<213> ORGANISM: Artificial Sequence
<220> FEATURE:
<223> OTHER INFORMATION: STAT-1 Decoy

<400> SEQUENCE: 2
gatctaggga tttccgggaa atgaagct                                          28

<210> SEQ ID NO 3
<211> LENGTH: 16
<212> TYPE: DNA
<213> ORGANISM: Artificial Sequence
<220> FEATURE:
<223> OTHER INFORMATION: GATA-3 Decoy

<400> SEQUENCE: 3
agcttgagat agagct                                                       16

<210> SEQ ID NO 4
<211> LENGTH: 28
<212> TYPE: DNA
<213> ORGANISM: Artificial Sequence
<220> FEATURE:
<223> OTHER INFORMATION: STAT-6 Decoy

<400> SEQUENCE: 4
gatcaagacc ttttcccaag aaatctat                                          28

<210> SEQ ID NO 5
<211> LENGTH: 19
<212> TYPE: DNA
<213> ORGANISM: Artificial Sequence
<220> FEATURE:
<223> OTHER INFORMATION: AP-1 Decoy
```

```
<400> SEQUENCE: 5
agcttgtgag tcagaagct                                                    19

<210> SEQ ID NO 6
<211> LENGTH: 20
<212> TYPE: DNA
<213> ORGANISM: Artificial Sequence
<220> FEATURE:
<223> OTHER INFORMATION: Ets Decoy

<400> SEQUENCE: 6
aattcaccgg aagtattcga                                                   20
```